United States Patent
Larder et al.

(10) Patent No.: US 7,292,944 B2
(45) Date of Patent: Nov. 6, 2007

(54) ESTABLISHMENT OF BIOLOGICAL CUT-OFF VALUES FOR PREDICTING RESISTANCE TO THERAPY

(75) Inventors: Brendan Larder, Cambridge (GB); Richard P. Harrigan, Vancouver (CA); Kurt Hertogs, Antwerpen (BE)

(73) Assignee: Virco BVBA (BE)

( * ) Notice: Subject to any disclaimer, the term of this patent is extended or adjusted under 35 U.S.C. 154(b) by 293 days.

(21) Appl. No.: 10/399,412

(22) PCT Filed: Oct. 22, 2001

(86) PCT No.: PCT/EP01/12337

§ 371 (c)(1), (2), (4) Date: Apr. 17, 2003

(87) PCT Pub. No.: WO02/33402

PCT Pub. Date: Apr. 25, 2002

(65) Prior Publication Data

US 2004/0033489 A1   Feb. 19, 2004

Related U.S. Application Data

(60) Provisional application No. 60/241,836, filed on Oct. 20, 2000.

(51) Int. Cl.
*G06F 19/00* (2006.01)
(52) U.S. Cl. .................................................. 702/19
(58) Field of Classification Search ............ 702/19–29; 707/102
See application file for complete search history.

(56) References Cited

U.S. PATENT DOCUMENTS

| 6,103,462 | A | 8/2000 | Paulous et al. |
| 6,221,578 | B1 * | 4/2001 | de Bethune et al. ............ 435/5 |
| 2002/0064838 | A1 * | 5/2002 | Parkin et al. ............... 435/91.4 |
| 2003/0190603 | A1 * | 10/2003 | Larder et al. .................. 435/5 |
| 2003/0220777 | A1 * | 11/2003 | Kitchen et al. ............... 703/11 |

FOREIGN PATENT DOCUMENTS

| WO | WO 97/27319 A1 | 7/1997 |
| WO | WO 97/27480 A1 | 7/1997 |
| WO | WO 00/03511 A1 | 12/2000 |

OTHER PUBLICATIONS

The EuroGuidelines Group for HIV Resistance. AIDS 15(3) 309-320, 2001.*
Harrigan, P.R., et al. Baseline HIV drug resistance profile predicts response to ritonavir-saquinavir protease inhibitor therapy in a community setting. AIDS (London) Oct. 1, 1999, 13:1863-1871.*
Ioannidis, J. P. A. et al. Use of neural networks to model complex immunogenetic associations of disease . . . American Journal of Epidermiology (1998) vol. 147, No. 5 pp. 464-471.*
Guidelines for computer implemented inventions. Oct. 2005, copy not supplied. http://www.uspto.gov/web/offices/pac/dapp/opla/preognotice/guidelines101_20051026.pdf.*
Definition of Mantel-Haenszel test and odds ration meta analysis. StatsDirect, copyright 1990-2006, printed Mar. 13, 2006, http://www.statsdirect.com.*
Wolfe, R. Classic Statistics Lectures, Mantel-Haenszel methodology, Oct. 23, 2000.*
Wikipedia entry printed Mar. 13, 2006, Fisher's exact test, http://www.wikipedia.org.*
Hirsch, R. et al. Statistical First Aid ; Interpretation of Health Research Data, 1992 Blackwell Science, MA, Chapter 9, pp. 167-199.*
Rübsamen-Waitmann, et al., Resistance mutations selected in vivo under therapy with anti-HIV drug HBY 097 differ from resistance pattern selected in vitro, Antiviral Research vol. 42, 1999, pp. 15-24.

* cited by examiner

*Primary Examiner*—Lori A. Clow
(74) *Attorney, Agent, or Firm*—Woodcock Washburn LLP

(57) ABSTRACT

The present invention concerns methods and systems for improving the accuracy of predicting resistance of a disease to a therapy. In one embodiment of the invention, mean and standard deviation (SD) values of fold change in normalized sensitivity, relative to a laboratory wild type standard pathogen or malignant cell are calculated to demonstrate that the patient samples display inherently different degrees of variation in susceptibility to each therapy. In another embodiment, the 2×SD value for each therapy is used as the cut-off between sensitive (within normal susceptible range) and resistant (above normal susceptible range).

12 Claims, 7 Drawing Sheets

| DRUG | Previous Cut Off | New Cut Off |
|---|---|---|
| AZT | 4.0 | 4.0 |
| 3TC | 4.0 | 4.5 |
| ddI | 4.0 | 3.5 |
| ddC | 4.0 | 3.5 |
| d4T | 4.0 | 3.0 |
| ABC | 4.0 | 3.0 |
| NVP | 4.0 | 8.0 |
| DLV | 4.0 | 10.0 |
| EFV | 4.0 | 6.0 |
| IDV | 4.0 | 3.0 |
| RTV | 4.0 | 3.5 |
| NFV | 4.0 | 4.0 |
| SQV | 4.0 | 2.5 |
| APV | 4.0 | 2.5 |

FIGURE 4

| DRUG | Previous Cut Off (% Res) | New Cut Off (% Res) | Change (%) | Relative change |
|---|---|---|---|---|
| AZT | 33.5 | 33.5 | 0.0 | 0 |
| 3TC | 47.3 | 46.0 | -1.3 | -3 |
| ddI | 8.8 | 11.9 | 3.0 | 35 |
| ddC | 6.5 | 8.5 | 2.0 | 31 |
| d4T | 7.1 | 12.5 | 5.4 | 77 |
| ABC | 18.4 | 25.8 | 7.4 | 40 |
| NVP | 42.4 | 36.3 | -6.2 | -15 |
| DLV | 43.7 | 31.2 | -12.5 | -29 |
| EFV | 32.9 | 29.8 | -3.1 | -10 |
| IDV | 27.0 | 29.6 | 2.6 | 10 |
| RTV | 32.4 | 33.3 | 0.9 | 3 |
| NFV | 37.0 | 37.0 | 0.0 | 0 |
| SQV | 22.0 | 25.1 | 3.1 | 14 |
| APV | 12.6 | 19.3 | 6.8 | 54 |

FIGURE 5

ESTABLISHMENT OF BIOLOGICAL CUT-OFF VALUES FOR PREDICTING RESISTANCE TO THERAPY

RELATED APPLICATIONS

This Application is a National Stage Application under 35 U.S.C. § 371 of PCT/EP01/12337, filed Oct. 22, 2001, which claims priority benefit of U.S. Ser. No. 60/241,836, filed on Oct. 20, 2000, the contents of which are expressly incorporated herein by reference.

The present invention concerns methods and systems for improving the accuracy of predicting resistance of a disease to a therapy. More specifically, the invention provides methods for establishing the natural phenotypic variability in therapy resistance among individuals for available therapies which serve to establish biological cut-off values for phenotypic or genotypic resistance tests. The invention may be used in concert with any test or assay used to determine the phenotype or genotype of a disease. For example, the invention may be applied to tests that determine the resistance of a virus isolate to various antiviral drugs. The invention also relates to methods and systems for improving the accuracy of predicting a disease's clinical response to a particular therapy or combination of therapies.

As used herein, the term "disease" refers to a pathogen or malignant cell that causes a pathological condition in an organism from the pathogen's infection or malignant cell's replication. The term "pathogen", as used herein, includes but is not limited to bacteria, viruses such as human immunodeficiency virus (HIV), hepatitis C (HCV) or hepatitis B (HBV), prions, algae, fungi and protozoa. The term "malignant cells", as used herein, includes but is not limited to cells with malignant characteristics, growth transformed cells, cells that continue to grow past the point of contact inhibition, cells that divide with abnormally high frequency as compared to normal cells of the same type or cells that exhibit anaplasia, invasion and metastasis. A therapy, as used herein, refers to any animal, vegetable, mineral, pharmaceutical substance, form of radiation, or gene therapy used to treat a pathogen or malignant cell. It is understood that the term "active ingredient" refers to chemicals, drugs, thereof compounds, peptides, proteins, antibodies, aptamers, DNAs (including anti-sense DNA), RNAs, ribozymes and pharmaceutical acceptable compositions. A "patient sample" is defined as any sample obtained from an individual such as blood, serum plasma. Of this sample the pathogen may be used or proteins, or nucleic acids derived from said pathogen. A "reference sample" is defined as a standard laboratory reference pathogen such as for example the HIV LAI IIIB strain. "Susceptibility" or "sensitivity" to a therapy refers to the capacity of the disease, malignant cell, and/or pathogen to be affected by the therapy. "Resistance" refers to the degree to which the disease, malignant cell, and/or pathogen is unaffected by the therapy. The sensitivity, susceptibility or resistance of a disease towards a therapy may be expresssed by means of an $IC_{50}$ value. The $IC_{50}$ value is the concentration at which a given therapy results in a reduction of the pathogen's growth compared to the growth of the pathogen in the absence of a therapy. Resistance of a disease to a therapy may be caused by alterations in phenotype or genotype. Genotypic alterations include mutations, single nucleotide polymorphisms, microsatellite variations, epigenetic variations such as methylation. Phenotypic variations may be effected by genotypic variations or by post-translational modification.

Techniques to determine the resistance of a disease to a therapy are becoming increasingly important. Since the issuance of the first report suggesting a correlation between the emergence of viral resistance and clinical progression, techniques to determine the resistance of a pathogen or malignant cell to a therapy have been increasingly incorporated into clinical studies of therapeutic regimens. Brendan Larder et al., HIV Resistance and Implications for Therapy (1998), herein incorporated by reference. For example, as with viral infections, some studies also show that p53 mutations may also be predictive of tumor response to specific anticancer drug therapy, radiation treatment or gene therapy. This is the case in breast cancer where initial studies have shown that cisplatin and tamoxifen® are more effective in patients whose tumors have a p53 mutation. Thus, the aim of resistance monitoring is to provide the necessary information to enable the physician to prescribe the most optimal combination of therapies for the individual patient.

With more therapeutic options becoming available, phenotypic therapy resistance testing is expected to play an important role in the management and treatment of pathogen infection or cancer and the development of individualized treatment regimes [see e.g. Haulbrich et al. JAIDS, 2001, 26S1, S51-S59.]. Furthermore, the number of drug resistant diseases also increases. Phenotyping methodologies measure the ability of a pathogen or malignant cell to grow in the presence of different therapy(s) in the laboratory. This is usually expressed as the fold-change in the $IC_{50}$ or $IC_{90}$ values (the $IC_{50}$ or $IC_{90}$ value being the therapy concentration at which 50% or 90% respectively of the population malignant cells is inhibited from replicating). A highly resistant malignant cell might show a 50 or 100-fold increase in $IC_{50}$, for example. Some mutations only increase the $IC_{50}$ by as little as 2-3 fold. Unlike genotyping, phenotyping is a direct measure of susceptibility, reflecting the effects and interactions of all the mutations, known or unknown, on the behavior of the malignant cell population in the presence of therapy(s). On the other hand the cut-of value may be used to indicate hypersensitivity of a pathogen towards a given therapy. It has been demonstrated that a combination of HIV mutations lead to hypersensitivity of the pathogen towards a given therapy.

Although phenotyping is considered the 'gold standard' of resistance testing, its utility is dependent on the "cut-off" value of the fold increase in for example the $IC_{50}$ at which a pathogen or malignant cell is considered resistant. The term "cut-off value", as used herein, refers to the change in susceptibility above which the pathogen or malignant cell is classed as having reduced susceptibility for a particular therapy. "Therapy resistance," as used herein, pertains to the capacity of resistance, sensitivity, susceptibility or effectiveness of the therapy against the pathogen or malignant cell. There has been recent debate regarding the relevance of cut-off values currently in use. For example, currently used virological cut-off values, are usually the same value for each therapy tested and are determined not by clinical criteria but, for example, by the assay variability seen on repetitive testing of a single wild type (wt) standard virus. Some virological cut-off values are clearly out of line with known response data. For example, indications of low level resistance to non-nucleotide reverse transcriptase inhibitors (NNRTIs) does not lead to blunted responses to therapy in previously untreated individuals (Harrigan et al, Bachelor et al., *4th International Workshop on HIV Drug Resistance and Treatment Strategies*, Sitges, Spain. Abstr. (2000).) Other assays have cut-off values that are primarily based on the reproducibility of the assay, are the same for each therapy, or are not related to whether a therapy might work against the pathogen or malignant cell in clinical practice and are, therefore, rather arbitrary.

SUMMARY AND DETAILED DESCRIPTION OF THE INVENTION

A solution to these problems of "cut-off" values involves new methods for establishing the natural phenotypic variability in therapy resistance among untreated individuals for available therapies, serving to generate biologically relevant cut-off values for a phenotypic resistance test. The resulting, newly defined cut-off values, herein termed biological cut-off values, are a more accurate reflection of natural variation in the population and may prove to be more predictive of clinical response than virological cut-off values.

In one embodiment of the invention, biological cut-off values are determined from the mean and standard deviation (SD) values of fold change in sensitivity, also termed "fold resistance" herein, of patient samples relative to a laboratory wild type standard pathogen or malignant cell reference sample, which are calculated to demonstrate that the patient samples display inherently different degrees of variation in susceptibility to each therapy after raw data is normalized (e.g., log transformed). The mean and standard deviation may be calculated from any of the methods known to those of skill in the art.

In one embodiment the instant invention concerns a method for predicting resistance of a disease to at least one therapy, comprising:
  a) determining the sensitivity of a patient sample for said at least one therapy;
  b) determining the sensitivity of a reference sample for said at least one therapy;
  c) determining the patient fold resistance from the quotient of the sensitivity obtained in step a) over the sensitivity obtained in b);
  d) predicting resistance of a disease toward the at least one therapy by determining whether the patient fold resistance is above a cut-off fold resistance value,
    wherein the cut-off fold resistance value is determined from the mean and standard deviation of a distribution of patient fold resistance values for the at least one therapy determined for a group of patients According to the instant invention a group of patients useful to establish the distribution of fold resistances is 10 to 50 patients. Preferably a group of 50 to 500 patients may be used to determine the distribution of the fold resistances. More preferably a population of at least 500 patients is used to determine the distribution of the fold resistances. The distribution can be a normal distribution (Gaussian distribution) or can be a non-normal distribution. The non-normal distribution may be transformed to obtained a normal distribution.

In some embodiments, the patient samples are treatment naïve. The treatment naïve samples may also include pathogenic material, such as genetic material, that is predicted to be wild-type, or that is classed as wild-type by those in the art on the basis of its known sequence.

In some embodiments, at least about the mean fold increase in sensitivity+2×SD value for each therapy is used as the cut-off between sensitive (within normal range) and resistant (above normal range) after raw data is normalized. Thus, in some embodiments, the 2×SD value, which is equivalent to the 95% upper confidence limit on a Gaussian distribution, may be used as the cut-off fold resistance value.

(See FIG. 1). In this latter case 97.5% of the increases in fold resistance will be below this 95% upper confidence interval. In other embodiments, a higher confidence limit, such as the 97.5% upper confidence limit may be used as the cut-off value.

In some embodiments of the invention, the method may be used to determine the fold resistance for several, or all, available therapies for a disease.

The invention may be used with any of the diseases and therapies provided in the above definitions. For example, it may be used to predict resistance to one or more therapies to a pathological condition caused at least in part by a pathogenic infection or malignant cell replication.

Essential in therapy monitoring is deciding whether therapy is still effective. This decision relies on comparing the drug effect at the patient borne target with a reference target. This comparison provides a quotient of the effect at the patient target over the reference. Often this is expressed as a fold increase in resistance, wherein resistance can be expressed by means of an $IC_{50}$ value. The $IC_{50}$ can be the concentration at which the drug reduces the activity of the target by half compared to the activity of the target without inhibitor. The decision whether a compound or a drug is still effective resides in the cut-off i.e. a defined increase in $IC_{50}$. This cut-off is often based on the variability of the assay. This provides a cut-off that depends largely on the analytical performance of the assay. This approach suffers from the limitation that it does not consider the population based variation in drug responsiveness. In addition, such approach does not account for the different responsiveness towards different therapy regimens.

Since the current approaches do not account for the population based variability in resistance sensitivity, we determined the mean fold change in $IC_{50}$ in a mixed population of untreated patients to provide a biological distribution of the fold changes in $IC_{50}$. A mixed population is not restricted to e.g. a single gender, age, race, sexual behavior. Secondly, the method of the instant invention accounts for the different responsiveness in a population towards different drugs. Therefor the drug specific cut-off values determined by the instant approach, are more reliable parameters in estimating resistant over sensitive patients. In a further approach, the population based mean fold increase in cut-off was determined in patients bearing a wild type sequence. This further refinement accounts for potential bias in the fold increase in resistance due to potential treatment resistant individual in the population evaluated. Unexpectedly, the results from both approaches i.e. phenotyping in treatment naïve patients and virtual phenotyping in a population under treatment but still having a wild type pathogen, yielded similar mean fold changes in resistance for each evaluated HIV drug.

Any method capable of measuring changes in the ability of a pathogen or malignant cell to grow in the presence of a therapy(s) can be used in the present invention. Such methods of phenotyping include all methods known to persons of skill in the art. Known genotyping methods may also be used in the present invention.

For example and by way of illustration, methods for phenotyping bacteria suitable for use in the present invention include, but are not limited to, measurement of inhibitory zone diameters (see, e.g., Guoming et al., *Sex. Transm. Dis.* 27(2):115-8 (2000), expressly incorporated herein by reference), calorimetric indicator methods (see, e.g., Lozano-Chiu et al., *Diagn. Microbiol. Infect. Dis.* 31(3): 417-24 (1998), expressly incorporated herein by reference), and broth macrodilution method (see, e.g., Iwen et al., *J. Clin. Microbiol.* 34(7):1779-83 (1996), expressly incorporated herein by reference).

As an additional illustrative example, methods for phenotyping viruses suitable for use in the present invention include, but are not limited to, plaque reduction assays, PBMC p24 growth inhibition assays (see, e.g., Japour et al., *Antimicrob. Agents Chemother.* 37:1095-1101 (1993); Kusumi et al., *J. Virol.* 66:875-885 (1992), both of which are expressly incorporated herein by reference), recombinant virus assays (see, e.g., Kellam & Larder, *Antimicrob. Agents Chemother.* 38:23-30 (1994); and Pauwels et al., *2nd International Workshop on HIV Drug Resistance and Treatment Strategies*, Lake Maggiore, Italy. Abstr. 51(1998), all of which are expressly incorporated herein by reference); the use of GFP as a marker to assess the susceptibility of anti-viral inhibitors (Marschall et al., Institute of Clin. and Mol. Virol., University of Erlanger-Nuremberg, Schlobgarten, Germany); and cell culture assays (Hayden et al., *N. Eng. J. Med.* 321:1696-702 (1989), herein incorporated by reference).

As yet another illustrative example and by way of illustration, methods for phenotyping malignant cells suitable for use in the present invention include, but are not limited to, flow cytometric assays (see, e.g., Pallis et al., *Br. J. Haematol.* 104(2):307-12 (1999); Huet et al., *Cytometry* 34(6): 248-56 (1998), both of which are expressly incorporated herein by reference), fluorescence microscopy (see, e.g., Nelson et al., *Cancer Chemother. Pharmacol.* 42(4):292-9 (1998), expressly incorporated herein by reference), calcein accumulation method (see, e.g., Homolya et al., *Br. J. Cancer.* 73(7):849-55 (1996), expressly herein incorporated by reference), and ATP luminescence assay (see, e.g., Andreotti et al., *Cancer Res.* 55(22):5276-82 (1995), expressly incorporated herein by reference).

Though the invention may be used with any phenotype or genotype measuring test or assay that determines resistance, the following descriptions are designed to further describe possible applications of the invention.

In one embodiment, the biological cut-off values may be used in concert with direct phenotype assays, for example, Antivirogram™ (Virco, Inc.; WO 97/27480, U.S. Pat. No. 6,221,578 incorporated herein by reference). This assay is a phenotypic resistance assay that measures, in controlled laboratory conditions, the level of resistance of the HIV derived from an individual patient to each of the anti-HIV therapies currently available. The resistant 'behavior' of the virus may be the combined result of the effects of many different mutations and the complex interactions between them, including genetic changes that have not even been identified yet. In other words, it is a direct measure of resistance.

The test provides a quantitative measure of viral resistance to all the available drugs. This is expressed in terms of the $IC_{50}$. This is then compared to the $IC_{50}$ for fully sensitive, non-mutated 'wild-type' virus. The resistance of the sampled virus to each therapy is then expressed in terms of a fold-change in $IC_{50}$ compared to wild type. The report enables physicians to identify the therapy(s) that are no longer active and helps in the selection of the optimal combination of drugs for the individual patient.

In one embodiment of the invention, the degree of resistance of thousands of samples from untreated patients is measured, as well as of genetically wild-type viruses (viruses without any resistance mutations). The average susceptibility of the viruses tested vary from drug to drug. A unique cut-off value for each therapy based on these biological data may be set, so that a result above the cut-off values means that the virus can be said to be above the normal sensitive range with a high degree of confidence. For example, in one embodiment the level of confidence may be 97.5%.

In another embodiment, the invention may also be used in concert with rules-based or other less direct systems of determining the therapy resistance phenotype of a pathogen or malignant cell. An example of a less direct system is the Virtual Phenotype ™(Virco, Inc.; PCT/EP01/04445, incorporated herein by reference). This system predicts viral therapy resistance based on genotypic information. For example the reverse transcriptase or protease genes of a virus e.g. HIV are sequenced and compared to wild type sequence to identify mutations in these genes.

The genetic code for the region involved in drug resistance is fed into a software system. This system identifies all the mutations that can affect resistance to each drug. It then interrogates a database of genotypes and phenotypes to find genotypes from previous samples that match these mutations. When all the matches have been identified, the software retrieves the phenotypes for these samples and produces a VirtualPhenotype ™ by calculating the average increase in resistance for each drug. The VirtualPhenotype ™ is typically based on data from hundreds or thousands of real phenotypes with the same patterns of mutations. In this example, an increase in the accuracy by which a virus'therapy resistance is determined, by use of biologically relevant cut-off values, translates into an increase in the accuracy of predicting a virtual phenotype for a new virus isolate based on its genotype. Finally, the cut-off values of this indirect system can be chosen to improve the specificity and/or sensitivity of the indirect system at predicting whether or not a sample is above or below the biologically relevant cut-off values In yet another embodiment, the invention may also be used in concert with other systems for determining phenotype from genotype information, such as neural networks that determine the therapy resistance phenotype of a pathogen or malignant cell based on its genotypic information. For example, a neural network may be used to model the relationship between genotype and phenotype the resistance testing (U.S. patent application Ser. No. 09/589,167 now U.S. Pat. No. 7,058,616 (PCT/EP01/0636 incorporated herein by reference). The neural network may be used to identify mutation(s) or mutation patterns that confer resistance to a therapy and defines the genetic basis of therapy resistance. For example, a data set of genotypic and phenotypic data is collected from a phenotype-genotype database. Each member of the data set corresponds to a genetic mutation that is correlated to a phenotypic change in therapy resistance.

The data set is divided into a training data set and a testing data set. After the network has been trained, the prediction rate or concordance rate of the network is determined from a test data set. Samples which give an incorrect prediction are removed from the test data set and placed into a second training data set. The second training data set comprises the first data training set plus any samples that gave an incorrect prediction from the test data set. The second training data set is then used to re-train the neural network. If necessary, this process can be repeated until the desired performance level is achieved. By re-training the neural network in this fashion, it is possible to increase the performance of the neural network. The accuracy of this application, because it relies on a database of genotype and phenotype information, is enhanced by improvements on determining phenotypic therapy resistance with the use of the present invention's biological cut-off values.

In one embodiment the instant invention concerns a diagnostic tool for determining the resistance of a patient to at least one HIV therapy comprising the cut-off fold resistance value for said at least one therapy as determined herein. The diagnostic tool includes phenotypic resistance tests such as the Antivirogram®, VirtualPhenotyping®, Phenosense.

The instant invention concerns methods to determine resistance towards HIV compounds such as tenofovir, lopinavir, and those compounds disclosed in WO 99/67417, EP-A-945443 and WO 00/27825. In particular, [3R-[3α(1S*,2R*),3αβ,6αβ]]-[3-[[(4-aminophenyl)sulfonyl](2-methylpropyl)amino]-2-hydroxy-1-(phenylmethyl) propyl] carbamic acid hexahydrofuro[2,3-b]furan-3-yl ester or 4-[[6-amino-5-bromo-2-[(4cyanophenyl)amino]-4-pyrimidinyl]oxy]-3,5-dimethyl benzonitrile or 4-[[4-[(2,4,6-trimethylphenyl)amino]-2-2pyrimidinyl]amino benzonitrile or any pharmaceutically acceptable salt or any stereoisomeric from thereof.

In one embodiment the effect of drugs on HBV may be monitored using technologies such as disclosed by Isom e. al. (WO 99/37821, Delaney et al. Antimicrob. Agents chemotherap. 2001, 45(6) 1705-1713).

In one embodiment the effect of drugs on HCV towards therapy may be determined using techniques such as described by Rice (WO 97/08310, WO 98/39031) and Barthenschlager (EP 1043399).

BRIEF DESCRIPTION OF THE FIGURES

FIG. 4: Comparison of old and new phenotypic cut-off values for anti-viral drugs.

FIG. 5: Effect of the new cut-off values on the prediction of resistance to antiviral drugs.

The following example is provided by way of illustration and is not intended to be limiting of the present invention.

EXAMPLE 1

Determination of Biologically Relevant Cut-Off Values for Different Anti-HIV Therapies.

Figure 1:
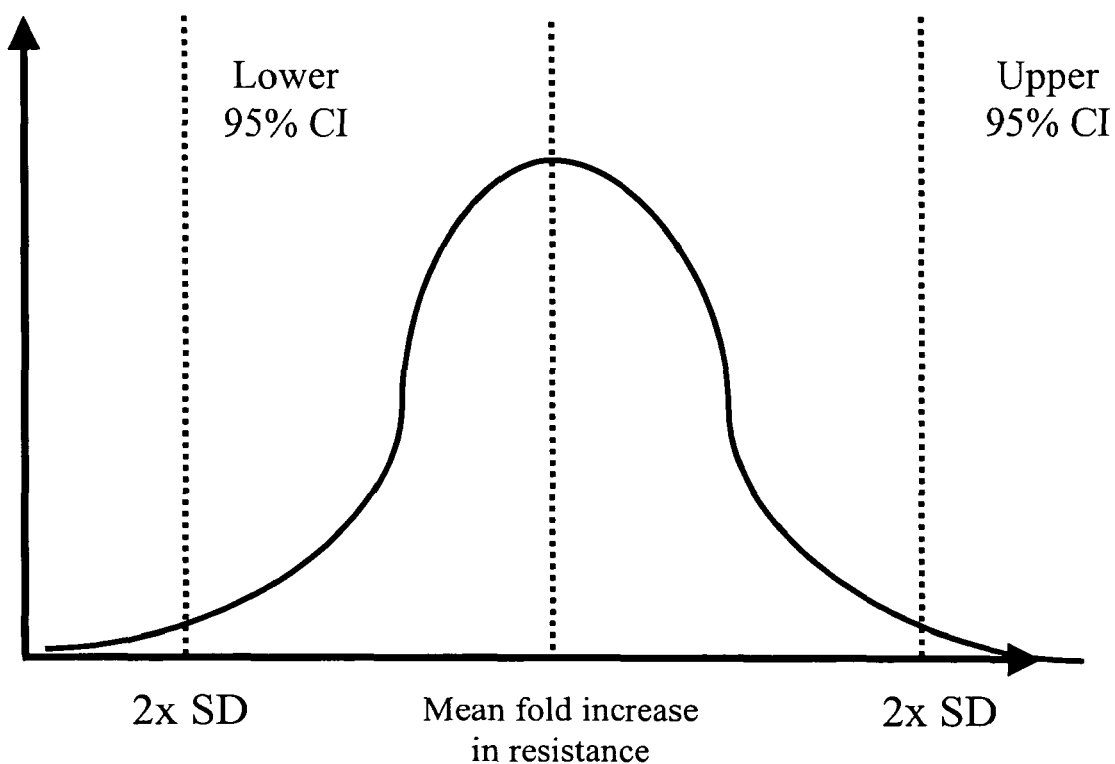
FIG. 1: Example curve showing the mean and 2× standard deviation of the fold change in drug sensitivity of a diverse set of patient samples for a given therapy.

Drug susceptibility of approximately 1000 geographically diverse untreated patient samples was determined for all currently approved antiretrovirals using the Antivirogram™ assay. Mean and standard deviation (SD) values of the fold change in sensitivity (log scale) of the patient samples relative to a laboratory wild type standard virus, demonstrated that the patient samples displayed inherently different degrees of variation in susceptibility to each drug (smallest variation with protease inhibitors (PIs) and greatest with the NNRTIs). The fold change in sensitivity of the samples to a drug is also termed the fold resistance of the samples to the drug. The 2×SD value for each drug was used as the cut-off between sensitive (within normal susceptibile range) and resistant (above normal susceptible range). Given this cut-off value, 97.5% of samples fall within a normal susceptible range while 2.5% were above normal range, indicating that untreated individuals will usually fall into the sensitive range. FIG. 1 represents an example of such an analysis for a single antiviral drug. These varied between 3-4.5 fold for the nucleosides, 6-10 fold for the NNRTIs and 2.5-4 fold for the PIs.

Figure 2:
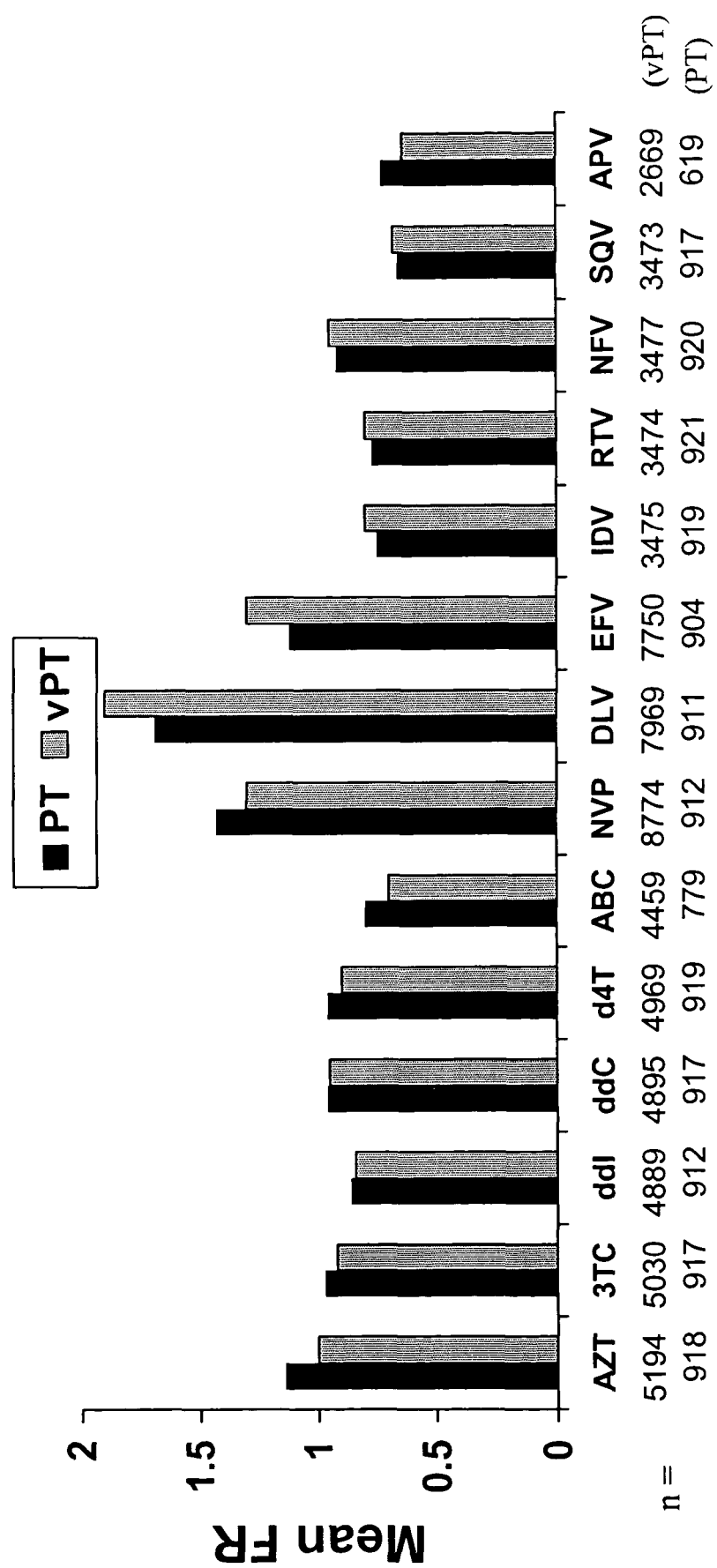
FIG. 2: The mean fold resistance (Mean FR) of patient samples to a variety of available anti-viral drugs. Data are calculated from both direct phenotyping of drug naïve patients (PT) and virtual phenotyping of patients with wild type-like virus currently taking drugs (vPT). N refers to the number of patient samples tested. The anti-viral drugs used are AZT, ddI, ddC, d4T, abacavir (ABC), nevirapine (NVP), delavirdine (DLV), efavirenz (EFV), indinavir (IDV), ritonavir (RTV), nelfinavir (NFV), saquinavir (SQV), and amprenavir (APV).

For cross validation, the mean fold resistance values for a large group of genotypically "wild type" samples were calculated (between 2100-7500 per drug). These values coincided almost exactly with the mean values derived from the untreated patient samples. Thus, the newly defined biological cut-offs were an accurate reflection of natural variation in the population and proved to be more predictive of clinical response than existing cut-off values. FIG. 2 contains the mean fold resistance values for several samples, employing both direct phenotyping (PT group) and virtual phenotyping methods (vPT group). A fold resistance of approximately one means that there is no difference with the wild type laboratory virus, thus the person is susceptible to therapy. The PT group represents drug naïve patients while the vPT group represents individuals who already take drugs but do not display mutations known to confer significant resistance upon genotyping (e.g. they resemble drug naïve patients).

Figure 3:
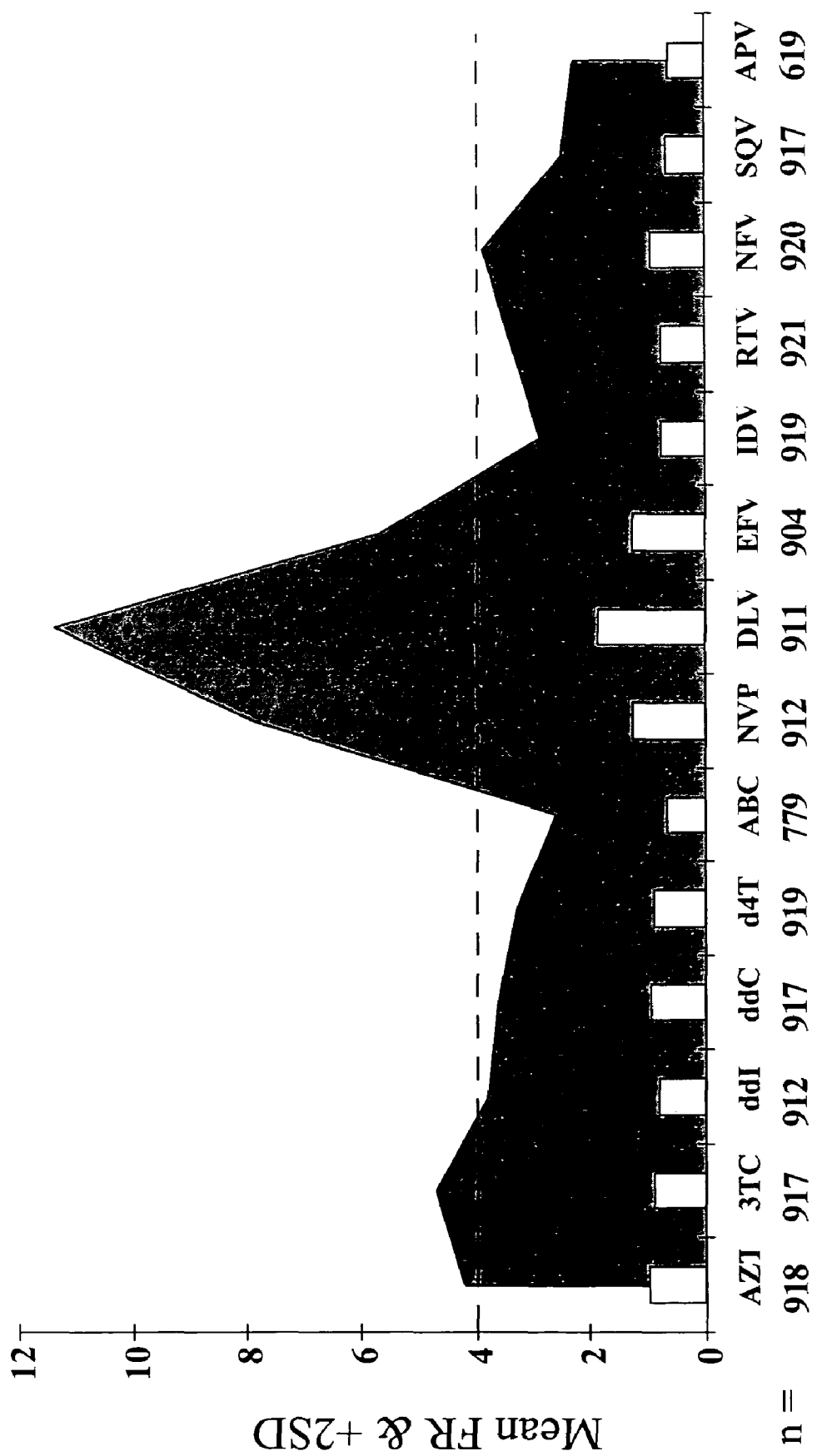
FIG. 3: Mean fold resistance (Mean FR) for patient samples compared with the 2× standard deviation (2SD) range. The dashed line at 4-fold increase in sensitivity is the previously used phenotypic cut-off value.

FIG. 3 demonstrates the mean fold resistance (light gray) found for the number of samples indicated at the bottom in the context of the 2×SD range (dark gray background). Several drugs differed from the arbitrarily chosen 4 fold increase in sensitivity, which was the phenotypic cut-off previously employed for this assay Although the relationship of the new cut-off values to clinical response is still under investigation, it was already apparent that modest increases in resistance to NNRTIs (around 2.5-5 fold) did not predict treatment failure. FIG. 4 contains a comparison of the old and new cut-off values. Worthy of note is the observation that delavirdine (DLV) shows an increase from 4 to 10, but this increase did not actually affect the decision of many samples. On the contrary, d4T, which showed a decrease in cut-off value resulted in a doubling of the number of resistant sample (see also FIG. 5). FIG. 5 shows the effect of the change in cut-off value (shown in FIG. 4) on the decision taken concerning resistance of the samples.

Figure 6:
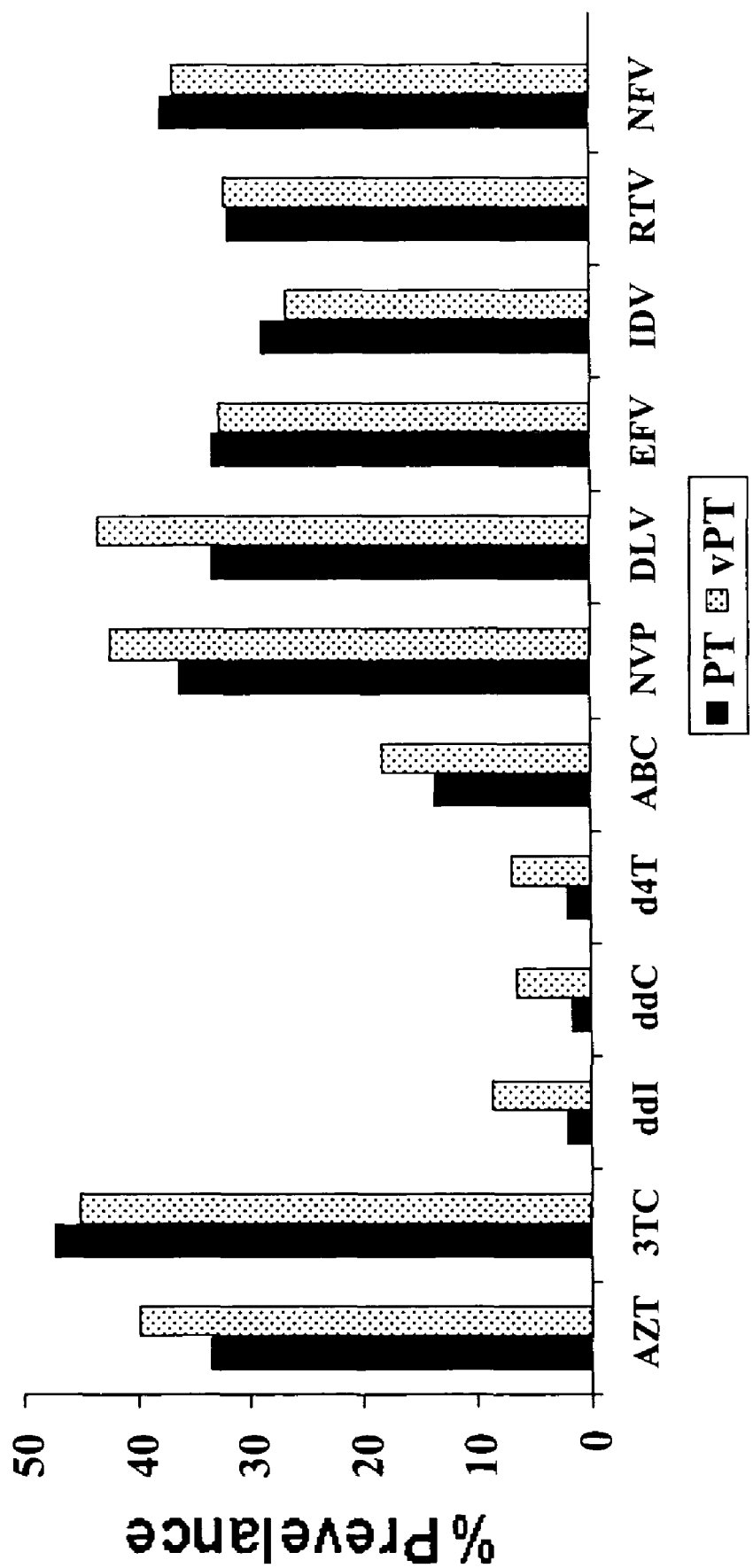
FIG. 6: Predicted resistance to anti-viral drugs predicted from phenotype (PT) and virtual phenotype (vPT) testing in 5000 samples without known drug resistance mutations using old cut-off values.
Figure 7:
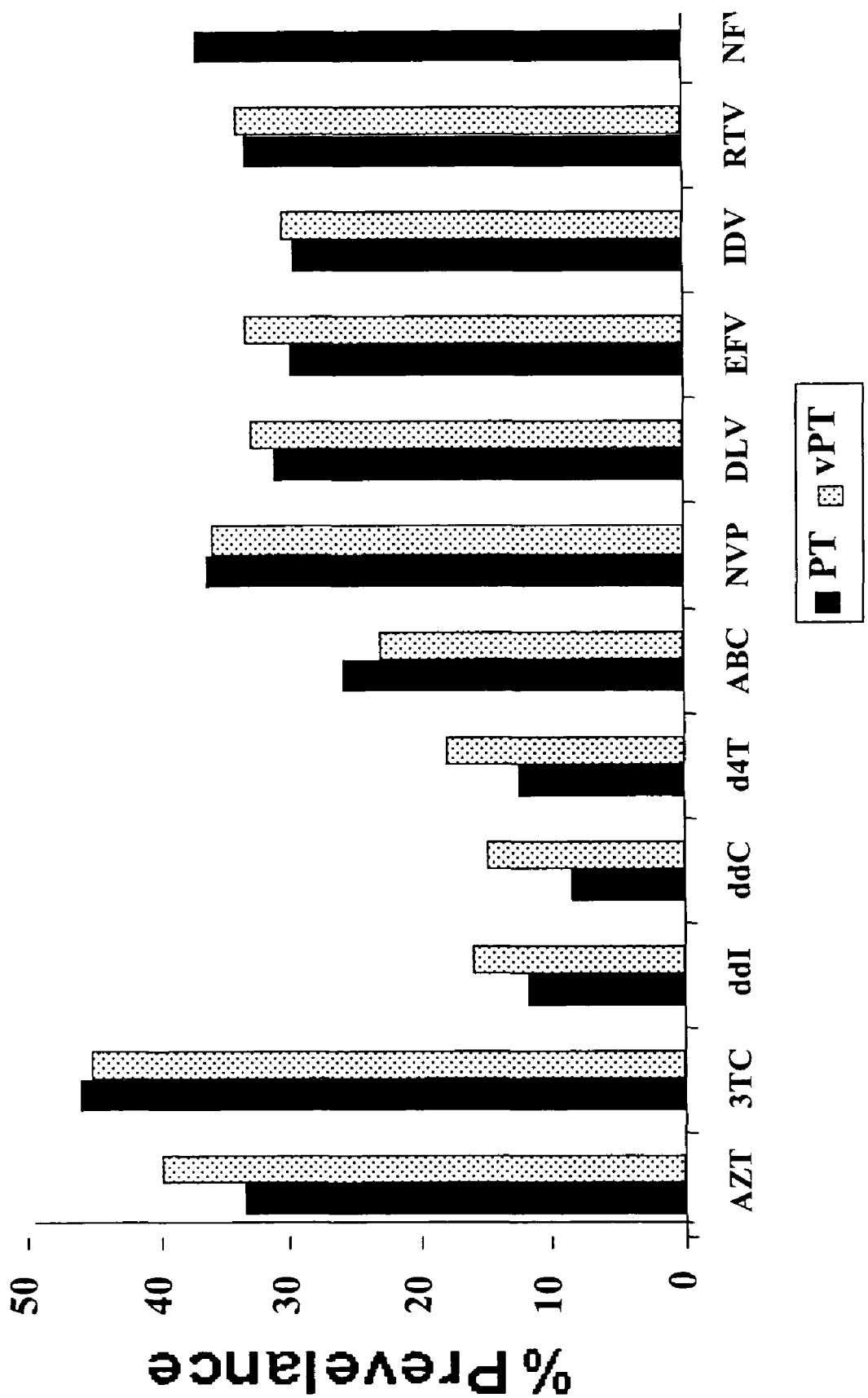
FIG. 7: Predicted resistance to anti-viral drugs predicted from phenotype (PT) and virtual phenotype (vPT) testing in 5000 samples without known drug resistance mutations using new cut-off values.

FIG. 6 shows the resistance called by both phenotype and virtual phenotype testing in 5000 samples without known drug resistance mutations. When compared with FIG. 6, FIG. 7 demonstrates that the new biological cut-off values yield a better concordance between virtual phenotyping and direct phenotyping.

All patents, patent applications and references referred to are incorporated herein by reference in their entirety.

The invention claimed is:

1. A method for determining the resistance of a patient to at least one HIV therapy comprising determining a cut-off fold resistance value for said at least one HIV therapy as determined according to a method for predicting resistance of an HIV infection to at least one HIV therapy, comprising:
    a) determining a sensitivity of a patient sample for said at least one HIV therapy, wherein the sensitivity of the patient sample is determined by performing at least one of a phenotyping assay and a genotyping assay;
    b) determining a sensitivity of a reference sample for said at least one HIV therapy, wherein the sensitivity of the reference sample is determined by performing at least one of a phenotyping assay and a genotyping assay;
    c) determining a patient fold resistance from a quotient of the sensitivity obtained in step a) over the sensitivity obtained in b);
    d) predicting the cut-off fold resistance of a disease toward the at least one HIV therapy by determining whether the patient fold resistance is above a cut-off fold resistance value,
    e) wherein the cut-off fold resistance value is determined from the mean and standard deviation of a distribution of patient fold resistance values for the at least one HIV therapy determined for a group of patients
    f) thereby determining the resistance of the patient to at least one HIV therapy.

2. The method of claim 1, wherein the patient samples are treatment naive.

3. The method of claim 1, wherein the cut-off fold resistance value is determined as the mean of patient fold resistance values plus two times the standard deviation of the distribution of patient fold resistance values.

4. The method of claim 1, wherein the phenotyping assay includes at least one of plaque reduction assays, peripheral blood mononuclear cell p24 growth inhibition assays, recombinant virus assays, green fluorescent protein marker assays, and cell culture assays.

5. The method of claim 1, wherein the therapy is antiviral therapy.

6. The method of claim 5, wherein the therapy comprises protease inhibitor therapy.

7. The method of claim 5, wherein the therapy comprises reverse-transcriptase inhibitor therapy.

8. The method of claim 7, wherein the reverse-transcriptase inhibitor therapy comprises non-nucleoside reverse-transcriptase inhibitor therapy.

9. The method of claim 5, wherein the therapy includes treatment with at least one of AZT, ddI, ddC, d4T, abacavir, nevirapine, delavirdine, efavirenz, indinavir, ritonavir, nelfinavir, saquinavir, amprenavir, lopinavir, and tenovir.

10. The method of claim 5, wherein the therapy comprises at least one of envelope inhibitor, fusion and integrase inhibitor treatment.

11. A method for determining the resistance of a patient to at least one HIV therapy comprising determining a cut-off fold resistance value for said at least one HIV therapy as determined according to a method for predicting resistance of an HIV infection to at least one HIV therapy, comprising:
    a) determining a sensitivity of a patient sample for said at least one HIV therapy; wherein the sensitivity of the patient sample is determined by performing at least one of a phenotyping assay and a genotyping assay;
    b) determining a sensitivity of a reference sample for said at least one HIV therapy; wherein the sensitivity of the reference sample is determined by performing at least one of a phenotyping assay and a genotyping assay;
    c) determining a patient fold resistance from a quotient of the sensitivity obtained in step a) over the sensitivity obtained in b);
    d) predicting the cut-off fold resistance of a disease toward the at least one HIV therapy by determining whether the patient fold resistance is above a cut-off fold resistance value,
    e) wherein the cut-off fold resistance value is determined from a percentile value of a distribution of patient fold resistance values for the at least one HIV therapy determined for a group of patients
    f) thereby determining the resistance of the patient to at least one HIV therapy.

12. A method for determining the resistance of a patient to at least one HIV therapy comprising determining a cut-off fold resistance value for said at least one HIV therapy as determined according to a method for predicting resistance of an HIV infection to at least one HIV therapy, comprising:
    a) determining a sensitivity of a patient sample for said at least one HIV therapy, wherein the sensitivity is determined by performing a phenotypic assay wherein the value is expressed as an $IC_{50}$ value;
    b) determining a sensitivity of a reference sample for said at least one HIV therapy, wherein the sensitivity is determined by performing a phenotypic assay wherein the value is expressed as an $IC_{50}$ value;
    c) determining a patient fold resistance from a quotient of the sensitivity obtained in step a) over the sensitivity obtained in b);
    d) predicting the cut-off fold resistance of a disease toward the at least one HIV therapy by determining whether the patient fold resistance is above a cut-off fold resistance value,
    e) wherein the cut-off fold resistance value is determined from the mean and standard deviation of a distribution of patient fold resistance values for the at least one HIV therapy determined for a group of patients
    f) thereby determining the resistance of the patient to at least one HIV therapy.

* * * * *